US00PP20215P2

(12) United States Plant Patent
Klemm

(10) Patent No.: US PP20,215 P2
(45) Date of Patent: Aug. 11, 2009

(54) ***LOBELIA* PLANT NAMED 'KLELE07247'**

(50) Latin Name: *Lobelia erinus*
Varietal Denomination: KLELE07247

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,134

(22) Filed: Apr. 9, 2008

(51) Int. Cl.
*A01H 5/00* (2006.01)

(52) U.S. Cl. ..... Plt./451

(58) Field of Classification Search ..... Plt./263, Plt./451

See application file for complete search history.

*Primary Examiner*—Susan B McCormick Ewoldt
(74) *Attorney, Agent, or Firm*—Jondle & Associates, P.C.

(57) ABSTRACT

A new cultivar of *Lobelia* particularly characterized by light-blue flowers with white eyes, good tolerance to heat and a medium-vigorous growth habit with an upright plant habit and very good branching, is disclosed.

1 Drawing Sheet

Genus and species: *Lobelia erinus.*
Variety denomination: 'KLELE07247'.

BACKGROUND OF THE NEW PLANT

The present invention comprises a new and distinct cultivar of *Lobelia*, botanically known as *Lobelia erinus,* and hereinafter referred to by the cultivar name 'KLELE07247'. 'KLELE07247' originated from an open-pollination made in May 2003 in Stuttgart, Germany between the proprietary female *Lobelia* plant, '040312' (unpatented) and the male plant, an unnamed individual *Lobelia* plant (unpatented). A single plant selection was subsequently chosen for further evaluation and for asexual propagation.

The new cultivar was created in 2003 in Stuttgart, Germany and has been asexually reproduced repeatedly by vegetative cuttings and in-vitro propagation in Stuttgart, Germany over a three-year period (about 7 generations). 'KLELE07247' has been found to retain its distinctive characteristics through successive asexual propagations.

Plant Breeder's Rights for this cultivar were applied for in Switzerland on Jul. 26, 2007. 'KLELE07247' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Light-blue flowers with white eyes;
2. Good tolerance to heat; and
3. Medium-vigorous growth habit with an upright plant habit and very good branching.

DESCRIPTION OF THE PHOTOGRAPH

This new *Lobelia* plant is illustrated by the accompanying photograph which shows a close-up of the mature flowers, buds and foliage; the colors shown are as true as can be reasonably obtained by conventional photographic procedures. The photograph is of a plant about 3-months old and grown from rooted cuttings in 10-cm pots in a greenhouse (glasshouse) in Stuttgart, Germany in the spring under conditions which approximate those generally used in commercial practice.

DESCRIPTION OF THE NEW CULTIVAR

The following detailed descriptions set forth the distinctive characteristics of 'KLELE07247'. The data which define these characteristics were collected from asexual reproductions carried out in Stuttgart, Germany. The plant history was taken on 2-month old plants in 10-cm pots that were pinched once and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Campanulaceae.
- *Genus and species.*—*Lobelia erinus.*
- *Common name.*—*Lobelia.*

Parentage:
- *Female parent.*—The proprietary *Lobelia* plant '040312' (unpatented).
- *Male parent.*—An unnamed individual *Lobelia* plant (unpatented).

Plant:
- *Growth and branching habit.*—Medium-vigor, good branching.
- *Form.*—Upright.
- *Height* (*measured from the top of the soil, including any flowers*).—20 cm.
- *Width* (*horizontal plant diameter, including any flowers*).—28 cm.
- *Time to produce a finished flowering plant.*—9 weeks.
- *Outdoor plant performance.*—Very good.

*Time to initiate roots.*—3 weeks.
*Root description.*—Fine, white, moderate branching.

Stems:
*Length.*—About 20 cm.
*Diameter.*—0.15 cm.
*Internode length.*—2 cm to 4 cm.
*Color.*—RHS 137C.
*Texture.*—Slight pubescence, ribbed.
*Stem anthocyanin.*—Absent.
*Peduncle.*—Color: RHS 141B. Length: 2 cm to 3 cm. Diameter: 0.03 cm to 0.05 cm. Texture: Slight pubescence.

Leaves:
*Color, immature leaf.*—Upper surface: RHS 141A. Lower surface: RHS 141A and RHS 59B.
*Color, mature leaf.*—Upper surface: RHS 137A. Lower surface: RHS 137A and RHS 59B.
*Length.*—Basal leaves are 4 cm to 5 cm and upper leaves are 3 cm to 4 cm.
*Width.*—Basal leaves are 2 cm to 3 cm and upper leaves are about 1 cm.
*Shape.*—Basal leaves are elliptic and upper leaves are lanceolate.
*Margin.*—Serrate.
*Apex.*—Obtuse.
*Base.*—Acute.
*Texture* (*both surfaces*).—Smooth.
*Venation pattern.*—Pinnate.
*Venation color.*—RHS 144C.

Flower bud:
*Shape.*—Inverse drop.
*Diameter.*—0.4 cm to 0.6 cm.
*Length.*—1.0 cm to 1.2 cm.
*Color when bud is first starting to open.*—Greenish-white to bluish.

Inflorescence:
*Lastingness of individual blooms on plant.*—5 to 8 days.
*Fragrance.*—Absent.
*Inflorescence type.*—Raceme.
*Quantity of flowers and buds per flowering branch.*—10 to 15.

Flowers:
*Flower diameter* (*horizontal*).—About 2 cm.
*Flower height* (*vertical*).—About 2 cm.
*Immature flower.*—Color, upper and lower lobes: Upper surface: RHS 98C. Lower surface: RHS 98D.
*Mature flower.*—Upper lobe: Color: Upper surface: RHS 98C. Lower surface: RHS 98D. Length: 1 cm. Width: 0.6 cm. Shape: Obovate. Apex: Obtuse. Margin: Entire. Texture (both surfaces): Smooth. Lower lobes: Color: Upper surface: RHS 98C. Lower surface: RHS 98D. Length: About 0.6 cm. Width: About 0.2 cm. Shape: Obovate. Apex: Obtuse. Margin: Entire. Texture (both surfaces): Smooth.
*Corolla.*—Color: Inside: White with RHS 98B (blue) spots. Outside: White. Tube length: About 1 cm. Diameter: 0.3 cm.
*Calyx.*—Sepals: Color (both upper and lower surfaces): RHS 137C. Length: About 1.2 cm. Diameter: About 1.5 cm. Shape: Funnel, star-shaped (sepals are fused in the lower half). Apex: Acute. Texture: Upper surface has slight pubescence and lower surface is smooth.

Reproductive organs:
*Androecium.*—Number of anthers: 5. Filament length: About 0.7 cm. Filament color: Bluish-white. Pollen color: Dark yellow. Pollen amount: Abundant.
*Gynoecium.*—Pistil length: About 0.5 cm Stigma color: Dark violet. Style color: Light-green. Style length: About 1.0 cm.

Fruit and seed set: Seeds are small, round, 0.05 cm wide and dark brown/black in color.

Disease and insect resistance: Not observed.

COMPARISON WITH PARENTAL AND COMMERCIAL CULTIVARS

'KLELE07247' differs from the female parent, the proprietary *Lobelia* '040312' (unpatented) in that 'KLELE07247' an upright plant habit, while '040312' has a trailing plant habit. Additionally, 'KLELE07247' has a less vigorous growth habit than '040312'.

'KLELE07247' differs from the commercial comparison variety, 'Wesloarc' (U.S. Plant Pat. No. 15,871) in that 'KLELE07247' has a better branching habit than 'Hot Arctic'.

I claim:

1. A new and distinct cultivar of *Lobelia* plant as shown and described herein.

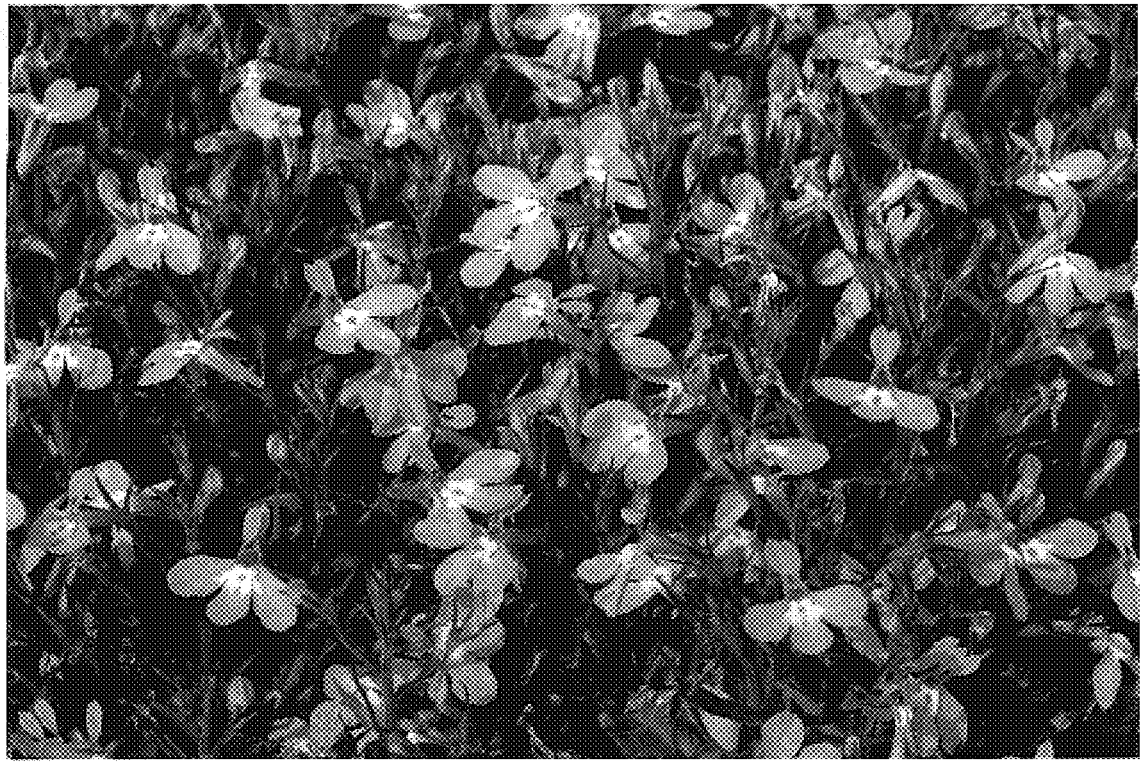

* * * * *